United States Patent [19]
Voss

[11] Patent Number: 4,986,110
[45] Date of Patent: Jan. 22, 1991

[54] METHOD AND APPARATUS FOR TAKING SAMPLES OF AND FOR ANALYZING HYDROCARBONS

[75] Inventor: Guenter Voss, Much, Fed. Rep. of Germany

[73] Assignee: Leybold Aktiengesellschaft, Fed. Rep. of Germany

[21] Appl. No.: 414,538

[22] Filed: Sep. 29, 1989

[30] Foreign Application Priority Data

Sep. 29, 1988 [EP] European Pat. Off. ............ 88116048

[51] Int. Cl.$^5$ ............................................. G01N 30/12
[52] U.S. Cl. ..................................... 73/23.38; 422/89
[58] Field of Search ...................... 73/23.1, 23; 422/89

[56]  References Cited

U.S. PATENT DOCUMENTS

| 4,102,647 | 7/1978 | Roelse et al. | 73/23.1 X |
| 4,541,268 | 9/1985 | Odernheimer | 73/23 |
| 4,865,996 | 9/1989 | Castleman et al. | 422/89 X |

FOREIGN PATENT DOCUMENTS 2496263 12/1980 France .
2008423  6/1979 United Kingdom .

OTHER PUBLICATIONS

N.T.I.S. Technical Notes, (1985) Sep., No. 9, Part J, Springfield, Va., "Novel Methane Gas Sensor Invented".

Primary Examiner—Hezron E. Williams
Assistant Examiner—Joseph W. Roskos
Attorney, Agent, or Firm—Hill, Van Santen, Steadman & Simpson

[57]  ABSTRACT

A method for taking samples of and for analyzing fluid hydrocarbons, whereby the sample is collected by sorption, is transported to an analysis equipment, and is analyzed; and an apparatus suitable for the implementation of this method. In order to implement sensitive analyses with adequately large sample quantities, the samples are collected by absorption in a solid sorbent having a high solubility and having a low diffusion quotient relative to the hydrocarbon samples.

16 Claims, 2 Drawing Sheets

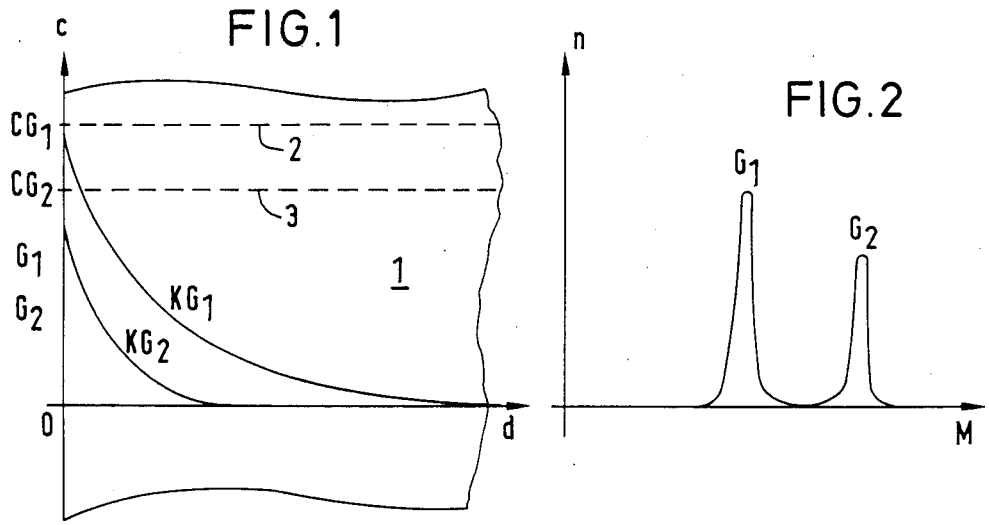
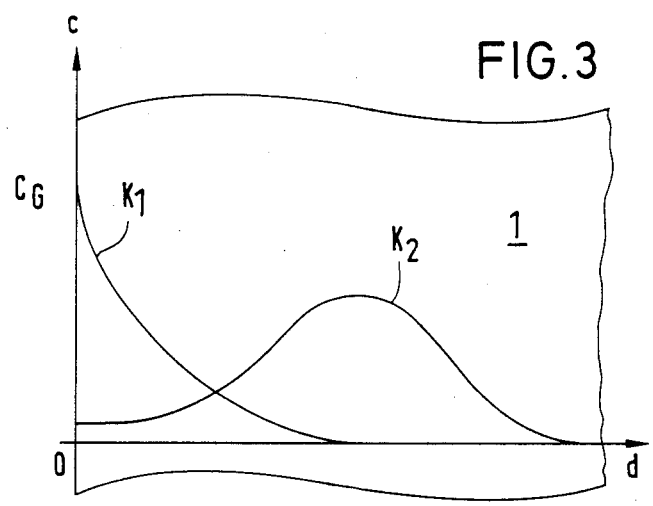
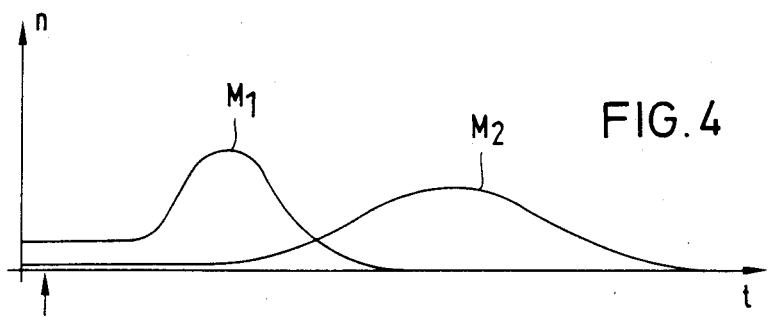

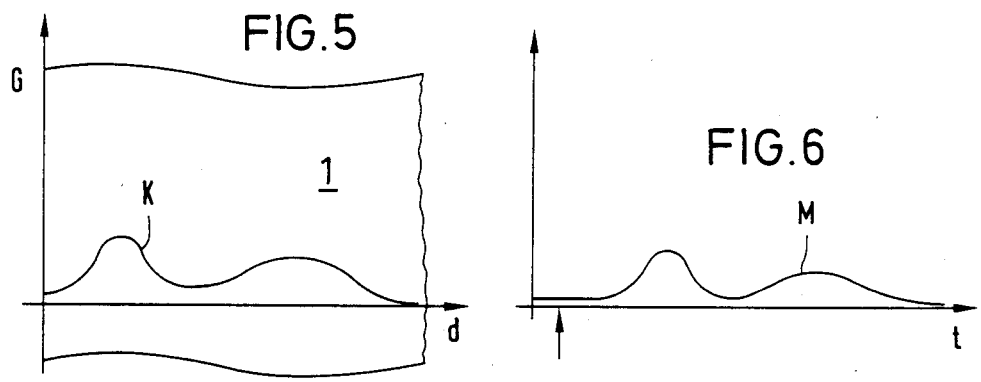
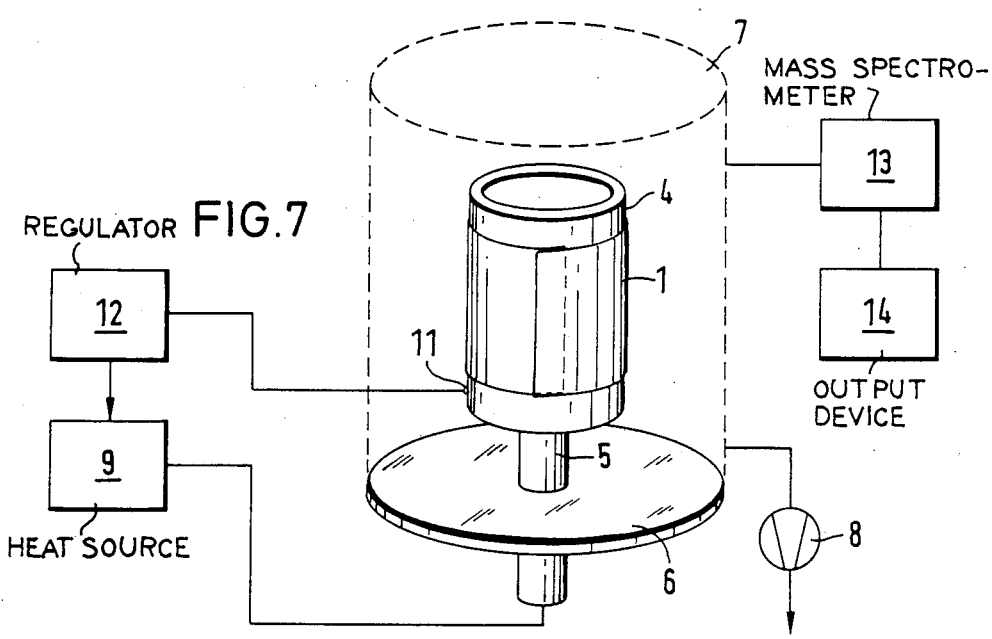
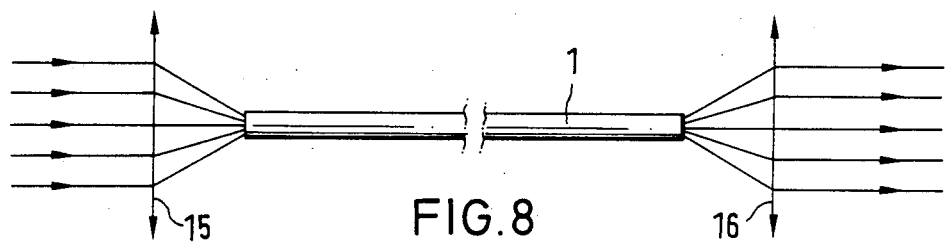

METHOD AND APPARATUS FOR TAKING SAMPLES OF AND FOR ANALYZING HYDROCARBONS

BACKGROUND OF THE INVENTION

The present invention is directed to a method for taking samples of and for analyzing fluid hydrocarbons, whereby the specimen is collected by sorption, is conveyed to an analysis means and is analyzed. The invention is also directed to a means suitable for the implementation of this method.

It is known that particularly volatile hydrocarbons frequently are the cause of serious environmental pollution; the specific effect of defined hydrocarbons on the environment, however, is still largely unexplored. Not the least of the reasons for this is that suitable sampling and analysis methods for fluid hydrocarbons are not yet available.

One method that is known is disclosed in "Staub, Reinhaltung der Luft", Vol 47 (1987), No. ½, pages 13 ff. In this method, gaseous samples are collected at the surface of adsorption agents present in powder or, respectively, granule form such as Tenax TA, Carbosieve S-II, and Molekularsieb 5A. However, this type of sampling does not make directly available high sample gas concentrations for the analysis step. Concentration of the collected hydrocarbons therefore follows the adsorption of the samples at the surface of the adsorption means. To that end, the hydrocarbons are thermically desorbed and are focused in a cooled capillary. A renewed thermic desorption then follows as does the delivery of the concentrated hydrocarbons to the analysis equipment (a capillary gas chromatograph).

SUMMARY OF THE INVENTION

The present invention provides an improved method for sampling hydrocarbons. The invention also provides an improved apparatus for implementing the method.

An object of the present invention is to simplify sample taking and to improve it such that adequately high sample concentrations are immediately available for the following analysis step, i.e., so that concentrating steps are no longer necessary.

To this end, the invention provides that samples are collected by sorption in a solid sorbent having relatively high hydrocarbon solubility and having a relatively low hydrocarbon diffusion quotient. As a consequence of the high solubility of the sorbent, it is possible to collect adequately large sample quantities for identification of elements by mass spectrometry or spectroscopic analysis methods. The low diffusion coefficient assures that the sorbent can satisfy a storing function, i.e. can simultaneously serve as a "sampling vessel" and as a conveying means to convey the samples from the sampling location to the analysis equipment.

The hydrocarbons to be investigated are usually gaseous. However, the invention can also be utilized for liquid samples.

A substance whose solubility $L$ ($cm^3/cm^3$ bar) is high enough so a sufficient dissolved sample quantity for identification is obtained given a justifiable sorbent volume, is suitable for use as a sorbent. Further, the diffusion coefficient $D$ ($cm^2/S$) must be small enough so that a relatively large dissolved sample quantity remains in the sorbent after sampling and is still adequate for identification analysis after being transported from the exposure/sampling location to the analysis equipment. It is thereby especially advantageous when the diffusion coefficient of the sorbent is extremely low.

Long-term observations thereby become possible without complete saturation of the hydrocarbons dissolved in the sorbent. Statements about the history of the exposure time can be made under these conditions.

Polymers such as polytetrafluorethylene-CO-Hexafluorpropylene (FEP) have proven especially suitable as sorbents for sampling in accordance with principles of the invention. Polymers of this type are obtainable as films in various thicknesses. FEP has extremely high solubilities for hydrocarbons (up to percentages of the film mass); while the diffusion coefficients are extremely low. The hydrocarbon components themselves can be so greatly enriched and stored in films having a thickness of 0.1 mm that the storage quantity is adequate for the mass analysis. FEP also has the advantage that it is chemically inert and can be manufactured with uniform structure (this being ideal for reproducibility of measurements). The employment of films having a thickness of 0.1 through 1 mm has proven advantageous.

Examples for D (diffusion coefficient) and L (solubility) in FEP include:

For $C_2H_6$:
$$D = 4.7 \times 10^{-9} \, cm^2 \cdot S^{-1}$$

$$L = 0.71 cm^3 \cdot cm^{-3} \cdot bar^{-1}$$

For $C_3H_8$:
$$D = 7.7 \times 10^{-10} cm^2 \cdot S^{-1}$$

$$L = 1.4 cm^3 \cdot cm^{-3} \cdot bar^{-1}$$

Fundamentally, all methods of gas analysis are suitable for the identification of the hydrocarbons dissolved in the sorbent since the stored gas quantities of the inventively taken samples are adequate for detection. Mass spectrometry methods (mass spectrometer, gas chromatograph, etc.) usually assume that the collected gas is thermically expelled before or during the analysis. Over and above this, the employment of FEP as a sorbent also has the advantage that photometrical methods can be employed for the identification of the hydrocarbons dissolved in the FEP as a consequence of the transmissivity of FEP (atom absorption spectrometer infrared equipment, etc.).

Further advantages and details of the invention will become apparent with reference to the following detailed description of the preferred embodiments and the accompanying drawings.

BRIEF DESCRIPTION OF THE DRAWINGS

FIG. 1 illustrates an edge of a sorbent exposed to a milieu of fluids;

FIG. 2 is a graph illustrating the mass spectrum for collected gases;

FIG. 3 illustrates the edge of the sorbent of FIG. 1 in magnified fashion;

FIG. 4 is a graph illustrating gas mass concentration over time during thermic heating;

FIG. 5 illustrates a gas concentration curve;

FIG. 6 illustrates a gas concentration over time during thermic heating; FIG. 7 illustrates an apparatus embodying principles of the invention wherein gas mass analysis is performed with simultaneous thermic heating of a sorbent; and FIG. 8 illustrates how samples can be scanned over their entire length when the sorbent is used as a light waveguide.

DETAILED DESCRIPTION OF THE PRESENTLY PREFERRED EMBODIMENTS

In FIG. 1, there is illustrated an edge of a sorbent 1, for example a polymer film, that is exposed to a milieu (for example, river water, stored wastes, foodstuffs, air, or the like) that is under investigation for the purpose of taking samples. The illustrated environment contains two hydrocarbon gases $G_1$ and $G_2$ having concentrations $CG_1$ and $CG_2$, respectively. The gas constituents of the milieu proceed into the polymer 1 via solvent diffusion, whereby the hydrocarbons—particularly if halogenated hydrocarbons—are preferred and, accordingly, diffuse with priority. Depending upon the solubility and diffusion coefficient, a defined quantity of the hydrocarbon gases are dissolved in the sorbent 1 after a defined time.

In FIG. 1, concentration curves $KG_1$ and $KG_2$ are superimposed on the illustrated edge of the sorbent 1. The concentration curves illustrate dissolved gas concentrations (c) over a thickness (d) of the film 1. The edge of the sorbent 1 is aligned with the y-axis (concentration) of the coordinate system.

After the exposure time, the sorbent 1 is transported from the exposure location to the analysis location. The gases $G_1$ and $G_2$ dissolved in the sorbent 1 are then thermically driven out in a vacuum and a mass analysis is simultaneously carried out. FIG. 2 shows the appertaining mass spectrum for the gases $G_1$ and $G_2$. Mass M is plotted versus signal amplitude n.

As a consequence of the high solubility of polymer films for hydrocarbon gases, a high gas quantity sufficient for mass analysis can be collected. Because of the low diffusion coefficient, the gas samples and can be stored over a long period of time because of the low diffusion coefficient. The storage time, moreover, can be extended by cooling the sorbent, for example during the time of transport from the exposure location to the analysis location.

The exposure time can be extended until a saturation of the gases dissolved in the sorbent 1 occurs. This condition is shown via broken lines 2 and 3 in FIG. 1. This would yield the advantage that the gas quantities dissolved in the sorbent 1 are extremely great; however, it would no longer be possible to make a statement about the history of the exposure time, as shall be set forth with reference to further figures.

FIG. 3 shows the edge of the sorbent 1 in greatly magnified fashion. The curve $K_1$ is a representative concentration curve that arises when a hydrocarbon gas G having a concentration $C_G$ at the exposure location was present during the entire exposure time. The curve $K_1$ is similar to the concentration curves $KG_1$ and $KG_2$ of FIG. 1. A quantitative statement about the concentration $C_G$ is possible when a mass spectrometer is set to the mass of the gas G and the mass spectrometer line is registered over the entire time of heating. The result is shown in FIG. 4 by way of curve $M_1$. An arrow A indicates the point in time at which heating began. The accelerated, thermic desorption begins after only a few seconds when the sorbent, or the film 1, has been subjected to an adequately high temperature (for example 200° C.). The heating process is maintained until the gas G is completely desorbed. The integral over the curve $M_1$ describes the total quantity of absorbed gas that—given knowledge of D, d, L, and the exposure time—is a measure of the concentration of the gas G at the exposure location.

A curve $K_2$ in FIG. 3 illustrates the concentration curve for the situation when the gas G was only temporarily present in the location of exposure. The concentration of this gas G is illustrated as having returned to zero during the exposure time. The concentration curve $K_2$ illustrates a maximum concentration in the interior of the sorbent or, respectively, of the film 1. As a consequence of the relatively low diffusion coefficient, the hydrocarbon molecules will therefore emerge later from the sorbent 1 during the thermic desorption than they would if they were situated in the edge region of the sorbent 1.

FIG. 4 includes an evaluation curve $M_2$ that corresponds to the concentration curve $K_2$. Compared to the curve $M_1$, the bell shape of the curve $M_2$ is displaced toward a longer time period. From the specific chronological curve, as depicted in FIG. 4, and given knowledge of the values of D, d, L and of the exposure time, the points in time for the beginning and end of the presence of the gas G can be reconstructed.

FIGS. 5 and 6 additionally illustrate the situation wherein a gas G was present in two different time spans during the exposure time of the film 1. By way of example, FIG. 5 shows a concentration curve for this case. FIG. 6 shows the course of the curve that is acquired upon thermic heating and simultaneously executed mass analysis. The times during which the gas G was present at the exposure location can be reconstructed from the course of the curve M.

FIG. 7 illustrates an apparatus for the implementation of the mass analysis given simultaneous heating of the film 1 in accordance with the invention. The film 1 is wound onto a cylindrical hollow member 4 that comprises relatively large-pore sintered material. The film 1 is fixed in the indicated position with a clamp (not shown). The sintered hollow member 4 is equipped with a heatable base 5 that is in turn secured to a flange 6. The flange 6 serves as a closure for a receptacle 7 (shown only by broken lines) that can be evacuated with the assistance of a vacuum pump 8.

A power source that supplies the heating is illustrated as a block 9. A temperature sensor 11 that supplies its signals to a regulator 12 is provided on the sintered member 4 in order to be able to carry out a temperature regulation program. The desired temperature curve can be set with the assistance of this regulator 12.

A mass spectrometer 13 is connected to the receptacle 7 during heating. Means for evaluating the signals supplied by the mass spectrometer 13 are illustrated by a block 14. Such means includes computers, printers, displays, and the like Between 200 nm and 8 um, FEP has a nearly constant transmissivity of more than 90%. It is thereby possible to also employ spectroscopic methods to identify the hydrocarbon masses. Oscillations of the collected hydrocarbons can be found within this window. The difference of the transmissivity up to 100% is attributed to reflection losses (there is a refractive index of 1.35). Accordingly, there is the possibility to also measure extremely long samples.

It can be appreciated from FIG. 8 that the samples to be investigated can be brought into a beam path over their entire length, i.e. the film 1 serving like a light conductor. Suitable coupling systems must be arranged preceding and following the film 1 (the thickness of which can amount to 0.1 through 1 mm and the length of which can amount to about 200 mm). All known methods are available for the spectroscopic detection itself.

Quantitative measurements and statements about the history of the exposure time of the film are similarly possible with these spectroscopic methods. This is possible if spectroscopic analyses are multiply carried out during the heating of the sorbent. Quantitative statements can be made and the chronological presence of the collected gases at the exposure location can be reconstructed in view of the disappearance of the absorption bands.

Due to enrichment mechanisms in the discussed methods, measurements can be carried out with high sensitivity. Additionally, sampling with solvent diffusion can be simply and comfortably interpreted in the laboratory.

Further, it can be appreciated that the method of the invention provides for the integral identification of concentrations of injurious substances in air as well as the monitoring of bodies of water. Thus, monitoring the overall exposure of persons who work in endangered areas is possible. The detection of minute quantities of fluoro or chloro hydrocarbons or tetrachloroethylene (for example, in foodstuffs) is possible.

While a preferred embodiment has been shown, modifications and changes may become apparent to those skilled in the art which shall fall within the spirit and scope of the invention. It is intended that such modifications and changes be covered by the attached claims.

I claim as my invention:

1. A method for taking samples of and for analyzing fluid hydrocarbons, comprising the steps of:
    collecting a hydrocarbon sample by sorption in a solid sorbent having a high solubility and having a low diffusion quotient with respect to the hydrocarbon sample;
    transporting the sample to analysis equipment; and
    analyzing the sample by heating the sorbent in a vacuum during the analysis and subjecting the sample to mass spectrometry.

2. The method of claim 1, wherein the step of analyzing the sample further comprises analyzing the sample before the sample has reached its solvent saturation in the sorbent.

3. The method of claim 1, wherein the step of analyzing is further defined by thermically desorbing the hydrocarbons dissolved in the sorbent, and conducting the analysis during the heating.

4. The method of claim 1, wherein the sorbent is a polymer film.

5. The method of claim 4, wherein tetrafluoroethylene-CO-hexafluorpropylene (FEP) film is used as the polymer film.

6. The method of claim 1, comprising the further step of bringing the film having the hydrocarbon sample to be analyzed into a beam path over a length of the film.

7. A method for taking samples of and for analyzing fluid hydrocarbons, comprising the steps of:
    collecting a hydrocarbon sample by sorption in a solid sorbent having a high solubility and having a low diffusion quotient with respect to the hydrocarbon sample;
    transporting the sample to analysis equipment;
    cooling the sorbent while being transported to the analysis equipment; and
    analyzing the sample.

8. An apparatus for analyzing samples collected in a sorbent, comprising:
    a vacuum chamber having a heatable carrier for the sorbent, the sorbent being made of a material having a high solubility and having a low diffusion quotient with respect to hydrocarbons; and
    a mass spectrometer connected to the vacuum chamber.

9. The apparatus of claim 8, wherein the sorbent is a polymer film.

10. The apparatus of claim 8, wherein the carrier includes means for regulating heating of the carrier.

11. The apparatus of claim 8, wherein the carrier comprises a sintered hollow member onto which the sorbent can be wound.

12. A method comprising the steps of:
    (a) providing a sorbent made of a tetrachloroethylene polymer film having a high solubility and a low diffusion coefficient with respect to hydrocarbons;
    (b) exposing the sorbent to a hydrocarbon;
    (c) absorbing the hydrocarbon in the sorbent;
    (d) transporting the sorbent to an analysis means; and
    (e) analyzing the sorbent to identify the hydrocarbon to which the sorbent was exposed.

13. The method of claim 12, comprising the further step of thermically desorbing the hydrocarbon from the sorbent during analysis.

14. A method, comprising the steps of:
    (a) exposing a sorbent to a hydrocarbon;
    (b) absorbing the hydrocarbon in the sorbent;
    (c) transporting the sorbent to an analysis means;
    (d) cooling the sorbent during transportation to the analysis means; and
    (d) analyzing the sorbent to identify the hydrocarbon to which the sorbent was exposed.

15. A method for taking samples of and for analyzing fluid hydrocarbons, comprising the steps of:
    collecting a hydrocarbon sample by sorption in a solid sorbent having a high solubility and having a low diffusion quotient with respect to the hydrocarbon sample;
    transporting the sample to analysis equipment;
    cooling the sorbent while being transported to the analysis equipment; and
    analyzing the sample.

16. A method for taking samples of and for analyzing fluid hydrocarbons, comprising the steps of:
    collecting a hydrocarbon sample by sorption in a solid sorbent made of a tetrafluoroethylene-CO-hexafluorpropylene (FEP) polymer film having a high solubility and having a low diffusion quotient with respect to the hydrocarbon sample;
    transporting the sample to analysis equipment; and
    analyzing the sample.

* * * * *